(12) United States Patent  
Santerre et al.

(10) Patent No.: US 8,954,298 B2
(45) Date of Patent: Feb. 10, 2015

(54) METHODS AND SYSTEMS FOR HELICOPTER ROTOR BLADE BALANCING

(75) Inventors: Arthur E. Santerre, Plymouth Meeting, PA (US); Sharyn E. Mlinar, Canton, OH (US)

(73) Assignee: The Boeing Company, Chicago, IL (US)

( * ) Notice: Subject to any disclaimer, the term of this patent is extended or adjusted under 35 U.S.C. 154(b) by 459 days.

(21) Appl. No.: 13/342,351

(22) Filed: Jan. 3, 2012

(65) Prior Publication Data

US 2013/0173224 A1    Jul. 4, 2013

(51) Int. Cl.
   *G06F 17/50*    (2006.01)

(52) U.S. Cl.
   CPC ...... *G06F 17/5086* (2013.01); *G01N 2223/646* (2013.01)
   USPC .......................................... 703/1; 244/17.11

(58) Field of Classification Search
   CPC .............................................. G01N 2223/646
   USPC ..................... 703/1; 244/17.11, 10
   See application file for complete search history.

(56) References Cited

U.S. PATENT DOCUMENTS

| | | |
|---|---|---|
| 5,475,622 A | 12/1995 | Reinfelder et al. |
| 5,824,897 A | 10/1998 | Beachum et al. |
| 7,905,031 B1 * | 3/2011 | Paulino ........................... 33/553 |
| 2008/0014091 A1 * | 1/2008 | Gentile et al. ............ 416/223 R |
| 2011/0109627 A1 * | 5/2011 | Zhang et al. .................. 345/420 |
| 2011/0320181 A1 * | 12/2011 | Pandey et al. ..................... 703/7 |

OTHER PUBLICATIONS

Juan D. Cuesta, "Modeling Helicopter Blade Dynamics Using a Modified Myklstad-Prohl Transfer Matrix Method" Naval Postgraduate School, Monterey California, Dec. 1994, 73 pages.*
Bielawa, Richard L. et al., Development of a System for Improved Helicopter Blade Tracking, Prepared for Aviation Applied Technology Directorate U.S. Army Aviation and Troop Command published Jun. 1995.
Branhof, Robert et al., Weight and Balance Measurement and Control for Helicopter Rotor Blades, presented Jun. 5, 2000.
Buckel, Joseph T., Rotor Blade Static Balance—Art or Science?, Technical Report published May 5, 2003.
Screen Capture from Avion AV Task website, http://www.avionavtask.com/USBF.html, downloaded Nov. 3, 2011.
Screen Capture from Rotor & Wing Aviation Services website, http://www.rwas.com.au/blade-balancing.html, downloaded Dec. 14, 2011.

* cited by examiner

*Primary Examiner* — Dwin M Craig
(74) *Attorney, Agent, or Firm* — DASCENZO Intellectual Property Law, P.C.

(57) ABSTRACT

Methods and systems for balancing helicopter rotor blades are disclosed. In some examples, density data of a rotor blade may be acquired by scanning the rotor blade. In some examples, a three-dimensional model of a rotor blade may be merged with density data of the rotor blade. In some examples, simulations may be performed to predict flight data associated with a modeled rotor blade. In some examples, a database may be referenced to predict a desired weight balance of a rotor blade.

20 Claims, 2 Drawing Sheets

METHODS AND SYSTEMS FOR HELICOPTER ROTOR BLADE BALANCING

FIELD

The present application relates to the balancing of helicopter rotor blades.

BACKGROUND

The balance, or weight distribution, of helicopter rotor blades affects the performance and stability of helicopters. Therefore, it is desirable for each of the several rotor blades of a helicopter to have similar weight distributions, because having non-uniform rotor blades may impart undesirable vibrations. Helicopter rotor blades often rotate in the range of 200-400 rpm during flight. At these rotational speeds, a small difference in weight distribution between rotor blades may have a significant effect on a helicopter's flight performance.

Rotor blades are in the shape of airfoils and may be described in terms of span and chord dimensions. The span of a rotor blade refers to the long, or longitudinal, dimension of the rotor blade, and the chord of a rotor blade refers to the short, or lateral, dimension of the rotor blade. Accordingly, the balance of a rotor blade may be described in terms of span-wise balance and chord-wise balance, with both affecting the overall balance and flight of a rotor blade.

Typically, a desired weight distribution, or balance, of a rotor blade is effectuated by appropriate placement of weights within the internal volume of the rotor blade. For example, one or more weights may be positioned selectively along the length of the rotor blade to effectuate a desired span-wise balance of the rotor blade. Additionally, one or more weights may be positioned selectively along the width of the rotor blade, typically at or near the outer tip of the rotor blade, to effectuate a desired chord-wise balance. Additionally or alternatively, rotor blade balance may be described in terms of the position of the center of gravity of the rotor blade, such as in terms of the span and chord dimensions of the rotor blade.

FIG. 1 schematically illustrates a portion of a rotor blade 10 of a BOEING® CH-47 CHINOOK™ helicopter. Specifically, FIG. 1 illustrates a portion of the tip of the rotor blade. The example of FIG. 1 is provided as an illustrative, non-exclusive example and does not limit the scope of the present disclosure. As seen in FIG. 1, the rotor blade defines a fore weight compartment 12 and an aft weight compartment 14. The fore weight compartment includes three rows of cylindrical weights 16 and spacers 18. Each row may be described as a weight package. The three packages are positioned laterally in the chord direction. Placement of the individual weights relative to the individual spacers along the longitudinal length of the packages affects the span balance, whereas placement of the weights relative to the spacers amongst the three packages affects the chord balance. In other words, placement of the weights and spacers in the fore compartment of the illustrated example may affect both the span balance and the chord balance of the rotor blade.

In the illustrated example, the aft weight compartment includes two rows, or packages, of cylindrical weights 16 and spacers 18, with the two packages being positioned vertically with respect to each other, or transverse with respect to the chord direction. Accordingly, placement of the weights relative to the spacers along the longitudinal length of the two packages in the aft weight compartment affects solely the span balance of the illustrated rotor blade. However, weights may be distributed between the fore weight compartment and the aft weight compartment to further adjust the chord balance of the illustrated rotor blade.

Traditionally, helicopter rotor blades may be balanced utilizing static testing and/or dynamic testing. Static testing typically includes placement of a rotor blade on a stand and measuring the weight of the rotor blade at various positions along the span and/or chord of the rotor blade. Such techniques are fairly successful in determining the span-wise balance of rotor blades but are less effective in determining the chord-wise balance of rotor blades. Moreover, static testing must be performed in a very controlled environment and often takes 2-8 hours or more solely to measure and adjust the balance of a single rotor blade.

Dynamic testing is more effective for chord-wise balancing of rotor blades, but requires the actual spinning of one or more rotor blades together with a master blade. A master blade is a rotor blade that has a desired balance to be matched by the rotor blade(s) being tested. Dynamic testing may be performed utilizing a helicopter itself or by installing a set of rotor blades in a whirl tower. A whirl tower is a controlled environment in which a full set of rotor blades may be installed and observed during rotation. During rotation of a set of rotor blades, including a master blade, the vertical position of the tips of the rotor blades may be observed and compared. A rotor blade that tends to climb, or whose tip is vertically above the tip of the master blade during rotation, is a result of weight positioned toward the aft of the tip relative to the chord-wise balance of the master blade. Conversely, a rotor blade that tends to dive, or whose tip is vertically below the top of the master blade, is a result of weight positioned toward the fore of the tip relative to the chord-wise balance of the master blade. Accordingly, based on observation of the relative tip heights of the rotor blades being tested, each rotor blade may be adjusted as desired. Dynamic testing of rotor blades requires trial and error and often requires several (e.g., five or more) flights, or tests, of a single rotor blade simply to adjust the chord-wise balance to a desired result. This amounts to approximately 2-8 hours or more per rotor blade being balanced.

The balancing of rotor blades is important both when they are manufactured as well as when they are serviced after use. Modern rotor blades typically are constructed of composite materials and therefore are highly repairable. That is, composite rotor blades, such as constructed of KEVLAR®, fiber glass, and other fiber and epoxy matrices, tend to be more easily patched than metal rotor blades, for example. However, repaired rotor blades are difficult to balance utilizing existing techniques, because of the high variability of the placement, sizes, and weights of patches and other structures used to repair rotor blades. Moreover, the chord-wise balance of a repaired rotor blade may be important not only at the tip of the rotor blade, but at various positions along the length of the span of the rotor blade.

SUMMARY

Methods and systems for balancing helicopter rotor blades are disclosed. Some methods according to the present disclosure include the processing of density data associated with a rotor blade to be balanced. In some examples, the density data may be acquired by scanning the rotor blade, such as with a computer densitometry system, computer tomography system, or an X-ray computed tomography system. The processed density data may be used to predict a desired weight distribution for a rotor blade to be balanced. Systems according to the present disclosure may include one or more of a computer, a scanner, and dynamic testing equipment, such as that may facilitate the various methods disclosed herein.

DESCRIPTION

Methods and systems for balancing helicopter rotor blades are disclosed herein. However, the methods and systems disclosed may find application outside of helicopter rotor blades, including (but not limited to) wind turbine rotor blades, rotor blades associated with other applications, and applications associated with structures other than rotor blades, such as that may require repair and/or balancing for optimum performance in their intended applications.

Figure 2:
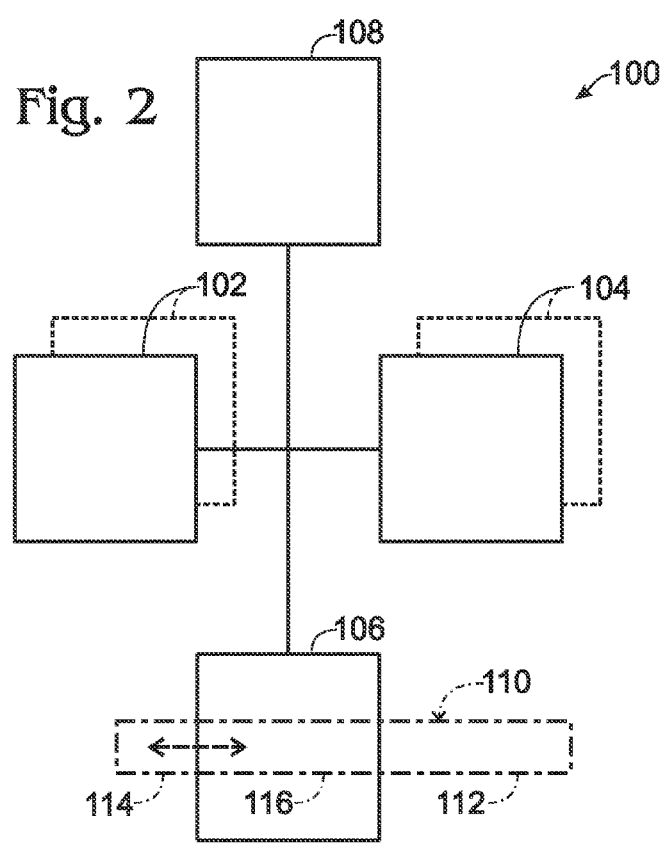
FIG. 2 is a schematic diagram representing illustrative, non-exclusive examples of systems according to the present disclosure for helicopter rotor blade balancing.

Examples of systems according to the present disclosure for balancing rotor blades are illustrated in FIG. 2 and are indicated generally at 100. The diagram of FIG. 2 is schematic in nature and is provided to broadly illustrate relative relationships between the illustrated structures, or subsystems, including optional structures and subsystems. FIG. 2 is not intended to be to scale or to require the illustrated relationship in all embodiments of systems 100. The schematic representations in FIG. 2 do not require that all structure shown is required in all embodiments of a system 100, and a component or subsystem of a system 100 may define independent inventive subject matter, separate and apart from a system 100. Additionally or alternatively, a schematically illustrated component, itself, as well as other components and structures disclosed and discussed herein, may be described as a system 100 according to the present disclosure.

As schematically illustrated in FIG. 2, a system 100 may include one or more of a computer 102, a server 104, a scanner 106, and dynamic testing equipment 108. A system 100 may include more than one computer 102, such as connected via a local area network. It is within the scope of the present disclosure that computer(s) 102 may be connected to server(s) 104, such as via a local area network or a wide area network. For example, server(s) 104 may be provided to maintain databases, to perform or assist in performing methods according to the present disclosure, to facilitate the transfer of data from one computer 102 to another, etc. It is within the scope of the present disclosure that one or more computers 102 may be located remotely from each other and be configured to, or be utilized to, perform methods and/or steps of methods according to the present disclosure. For example, as discussed herein, it is within the scope of the present disclosure that methods involving collected data may be performed by a computer 102; however, the computer 102 performing the method is not necessarily the same computer 102 that collected the data. Additionally or alternatively, a server 104 may be described as a computer 102 and vice versa.

Scanner 106 may be any suitable system that is capable of and configured to scan, or detect, desired properties of a helicopter rotor blade, or other structure depending on the application. Illustrative, non-exclusive examples of desired properties of a rotor blade may include (but are not limited to) one or more of the relative density of the rotor blade within various volumes of the rotor blade, surface contours of the rotor blade, and spatial relationships of the material or materials that define the rotor blade.

Illustrative, non-exclusive examples of suitable scanners 106 according to the present disclosure include (but are not limited to) computer densitometry systems, computer tomography systems, and X-ray computed tomography systems. Computer tomography systems, including X-ray computed tomography systems, additionally or alternatively may be referred to as CT scanners.

As schematically illustrated in FIG. 2, scanner 106 may be configured to scan, or otherwise acquire data associated with, a rotor blade 110, such as a helicopter rotor blade. The double-headed arrow in FIG. 2 schematically represents that the scanner may be configured to move relative to a rotor blade and/or may be configured to move (and/or permit movement of) a rotor blade relative to the scanner, for example, for purposes of acquiring data along the entire length, or span, or the rotor blade. It also is within the scope of the present disclosure, however, that a scanner 106 is configured to fully receive the entirety of a rotor blade 110 for purposes of scanning the rotor blade. For example, the scanner may include internal components that move relative to the rotor blade. Additionally or alternatively, depending on the type of scanner 106 utilized, the desired data may be acquired without moving the rotor blade relative to the scanner, or a subpart thereof, or vice versa.

As schematically indicated in FIG. 2, a rotor blade 110 may be described in terms of regions of the rotor blade, such as a hub region (or root-end) 112 corresponding to a region adjacent to the hub of a rotor when the rotor blade is installed, a tip region 114 corresponding to the opposite and distal end region of the rotor blade, and a body region 116 generally corresponding to the region of the rotor blade extending, or spanning, between the hub region and the tip region.

Some embodiments of scanners 106 may be described as industrial scanners, as opposed to medical scanners, which typically utilize very high resolution and slow scan rates. Scanners 106, on the other hand, in some embodiments may be described as low-resolution and/or as having a fast scan rate, at least relative to medical scanners and even typical industrial scanners used today. For example, scanners 106 may be configured to acquire data associated with a rotor blade at lower resolutions than at least one of 1, 10, 100, 1,000, or 10,000 microns. "At lower resolutions" refers to resolutions that are based on distances that are greater than the enumerated value. Additionally or alternatively, some embodiments of scanners 106 may be configured to acquire data at a rate of at least 15, 25, 50, 100, or 1,000 millimeters per minute. For example, in embodiments of scanners that move relative to a rotor blade, or vice versa, the rate of acquiring data may correspond to the rate of relative movement and thus may be described in terms of meters of the length, or span, or the rotor blade per second. Scan rates and resolutions that are less than, greater than, and within the various enumerated values herein also may be used and are within the scope of the present disclosure.

Depending on the configuration of scanner 106 utilized by a system 100 and/or utilized to perform, or at least partially perform, a method according to the present disclosure, the scanner may be configured to acquire density data of structure, such as a rotor blade, that is scanned by the scanner. As mentioned, however, scanners 106 may be configured to acquire other types of data associated with characteristics of scanned structures.

Dynamic testing equipment 108 may include any suitable testing and related equipment and instrumentation that may be utilized to test structure, such as a rotor blade, in a dynamic environment. For example, dynamic testing equipment 108 may include instrumentation, such as strain gauges configured to measure surface forces on a rotor blade and optical equipment (e.g., strobe cameras) configured to detect and/or facilitate detection of relative positions of rotor blades during rotation of a set of rotor blades, a whirl tower configured to rotate a set of rotor blades being tested, a helicopter configured to have installed a set of rotor blades being tested, vibration analysis instrumentation, etc. Any suitable equipment and instrumentation is within the scope of dynamic testing equipment 108, as may be appropriate for a particular test, to acquire particular desired data about a rotor blade or blades being tested, etc. In some systems 100, computer(s) 102 and/or server(s) 104 may be considered to be a component of or may be configured to work in conjunction with dynamic testing equipment 108.

Systems 100 and/or components or subsystems thereof, such as the components discussed herein with respect to FIG. 2, may be configured to utilize, implement, and/or otherwise facilitate various methods according to the present disclosure. As an illustrative, non-exclusive example, one or more of computer(s) 102 and/or server(s) 104 may be configured to implement methods or steps of methods according to the present disclosure, with such methods therefore being described as computer-implemented methods. Additionally or alternatively, one or more of computer(s) 102 and/or server(s) 104 may include, or be configured to read, computer readable storage, or memory, media suitable for storing computer-executable instructions, or software, for implementing methods or steps of methods according to the present disclosure. Examples of such media include CD-ROMs, disks, hard drives, flash memory, etc. As used herein, storage, or memory, devices and media having computer-executable instructions as well as computer-implemented methods and other methods according to the present disclosure are considered to be within the scope of subject matter deemed patentable in accordance with Section 101 of Title 35 of the United States Code.

Figure 3:
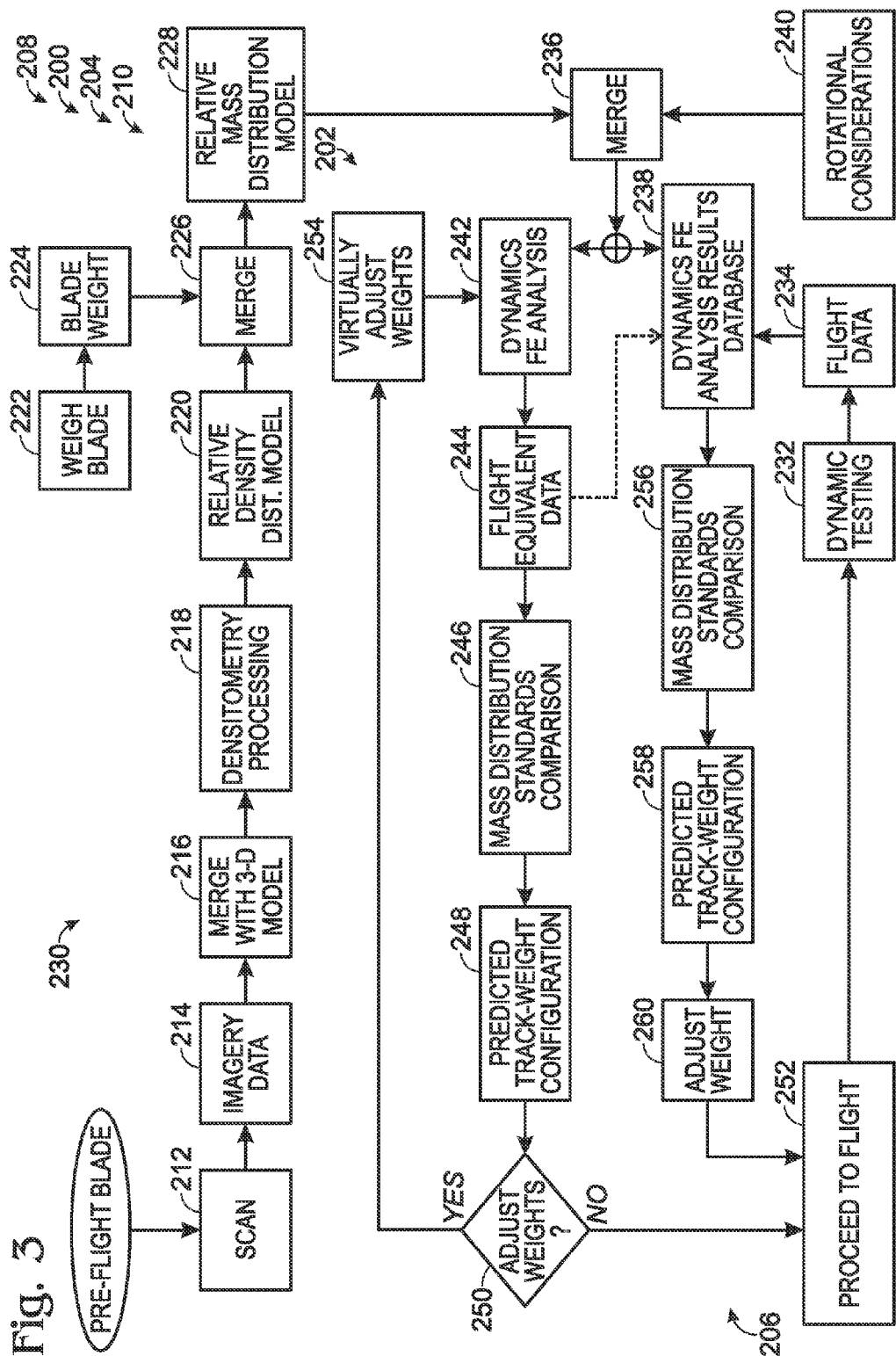
FIG. 3 is a flowchart schematically representing illustrative, non-exclusive examples of methods according to the present disclosure for helicopter rotor blade balancing.

FIG. 3 schematically represents illustrative, non-exclusive examples of methods, steps of methods, and results of steps of methods according to the present disclosure. FIG. 3 does not represent just a single method, but rather multiple methods according to the present disclosure that may include one or more of the schematically represented and discussed steps, standing alone, in combination, and/or with other steps and/or methods that are not expressly represented and/or discussed herein. While general flow, or timing, relationships between various steps are indicated by the directional arrow heads in FIG. 3, such relationships are not limiting in that such corresponding steps are not necessarily performed, or required to be performed, in the order illustrated.

As an illustrative, non-exclusive example, the schematic flowchart of FIG. 3 may be described in terms of methods of testing rotor blades, as generally indicated at 200, methods of balancing rotor blades, as generally indicated at 202, methods of building a database associated with balance data of rotor blades, as generally indicated at 204, methods of predicting the balance of rotor blades, as generally indicated at 206, methods of operating a rotor blade balance program, as generally indicated at 208, and/or methods of acquiring data associated with rotor blades, as generally indicated at 210. Other methods also are within the scope of the present disclosure as discussed herein.

Beginning first in the upper left corner of FIG. 3, a preflight rotor blade, such as a newly manufactured helicopter rotor blade or a repaired helicopter rotor blade, may be scanned, as indicated at 212. In some methods, such a rotor blade may be described as a rotor blade to be tested and/or a rotor blade to be balanced. Scanning step 212 may utilize a scanner 106 according to the present disclosure. In some methods, step 212 may be described as creating a low-resolution and/or high-speed scan of a rotor blade. Scanning step 212 additionally or alternatively may be described as acquiring data associated with a rotor blade, such as density data associated with a rotor blade.

As a result of the scanning step, imagery data may be acquired and/or produced, as indicated at 214. In methods in which density data is acquired, density data may be represented by (and/or the imagery data may be described as) a density map of the rotor blade, such as compiled, or otherwise constructed, by the scanner 106 or an associated computer 102. That is, it is within the scope of the present disclosure that a scanner 106 may be configured to produce the imagery data and/or that a computer 102 or server 104 may be configured to produce the imagery data based at least in part on the raw density data acquired by the scanner.

In some embodiments (although not required), the density map may be represented by, or may include, a raster image of the rotor blade, such as a three dimensional representation of the rotor blade represented by individual bits, or pixels, associated with volumes of the rotor blade at the resolution of the scanner or acquired data. In some such embodiments, the raster image may be a grayscale raster image. In some examples, depending on the configuration of scanner 106 utilized, the grayscale may correspond to mass absorption coefficients. In other words, the grey-scale may correspond to energy absorption and/or dispersion of the scanned rotor blade. A computer 102 may be configured to display the raster image on a display device and/or to store the raster image in memory.

Additionally or alternatively, and depending on the configuration of scanner 106 utilized, the imagery data and/or density map may be represented by, or may include, a three-dimensional construct of slices of the rotor blade at the resolution at which the scanner acquired the density data. Such slices generally may be two-dimensional or they may be three dimensional slices with generally parallel planar sides with a thickness corresponding to the resolution of the scanner. Other configurations and formats of representing imagery data and density maps are within the scope of the present disclosure, and systems and methods herein are not limited to the specifically described optional types of imagery data and density maps.

As indicated at 216, the imagery data may be merged with a three-dimensional model of the rotor blade, such as according to a finite element model composed of finite volumes within an outer contour of the rotor blade. For example, the merging of the imagery data and the three-dimensional model of the rotor blade may include merging corresponding slices of the imagery data with the volumes of the three-dimensional model.

Any suitable three-dimensional models of the rotor blade may be used, such as that include volumes of various shapes and sizes, one or more volumes corresponding to critical regions of the rotor blade, one or more volumes corresponding to repaired or refurbished regions of the rotor blade, one or more volumes corresponding to the hub region (or root-end) of the rotor blade, one or more volumes corresponding to the tip region of the rotor blade, and/or one or more volumes corresponding to the body region of the rotor blade. In some examples of three-dimensional models, volumes associated with a critical region may be smaller than volumes associated with a non-critical region. As used herein, a critical region of a rotor blade is a region of a rotor blade that may require precise balancing and/or whose balance more greatly affects the performance of the rotor blade than other regions of the rotor blade. For example, in some examples, repaired or refurbished regions of a rotor blade may be considered to be critical regions, and therefore may be modeled with smaller volumes than other regions of the rotor blade. Additionally or alternatively, the tip region of a rotor blade may be considered to be a critical region because of the dynamic effects that result from small differences in the balance of the tip region of a rotor blade and/or because of the placement of the weights that are used to adjust the balance of the rotor blade. For example, in some examples, the tip region of the rotor blade may be modeled with volumes that are at least as small as the balance weights that are installed in the tip region of the rotor blade. In some examples, a critical region may account for less than 10% or less than 5% of the overall span of the rotor blade. Other configurations also are within the scope of the present disclosure.

As indicated at 218, densitometry processing may be performed, for example, by a computer 102, to produce a relative density distribution model of the rotor blade, as indicated as 220. This processing may include assigning a density value to each volume of the finite volumes defined by the three-dimensional model, with these density values corresponding to the grey-scale of the raster image. The relative density distribution model therefore represents the relative densities between the volumes of the three-dimensional model of the rotor blade.

Subsequent to, prior to, or in parallel with the scanning of the rotor blade, the rotor blade may be weighed, as indicated at 222, resulting in a measured weight of the rotor blade, as indicated at 224. As indicated at 226, the weight of the rotor blade and the relative density distribution model of the rotor blade may be merged to arrive at a relative mass distribution model of the rotor blade, as indicated at 228.

Blocks 212-228 of FIG. 3, including the corresponding discussed methods, steps, models, etc., may be described as defining a method 230 of determining the mass distribution of a rotor blade.

As indicated at 236, some methods according to the present disclosure may include the merging of the relative mass distribution model of a rotor blade with rotational considerations 240 to arrive at a dynamic model of the rotor blade. These rotational considerations, for example, may include collective pitch angles at one or more rotational speeds.

As indicated at 242, a dynamic simulation of the modeled rotor blade may be performed, for example by a computer 102 operating dynamic simulation software. The dynamic simulation may result in predicted flight data, as indicated at 244. In other words, the simulation may result in a prediction of the flight characteristics of the modeled rotor blade without actually performing dynamic testing of the rotor blade. This data and its association to the modeled rotor blade may be saved in database 238 for future reference and comparison to subsequently modeled rotor blades.

Then, as indicated at 246, by comparing the modeled rotor blade and its predicted flight data to existing data associated with a desired rotor blade balance, such as associated with a master blade, a proposed configuration, or reconfiguration, of the rotor blade's balance weights may be achieved, as indicated at 248. In some cases, it may be that the balance of the modeled rotor blade already matches the desired balance of a master blade, in which case, the weights need not be (at least initially) adjusted. In other cases, it may be that the balance of the modeled rotor blade does need adjusting in an effort to match it to that of a master blade, or other desired balance configuration. These two options are indicated in FIG. 3 at 250, and as indicated, if no weight adjustment is required, the rotor blade may then proceed to installation on a helicopter and use in the field, to installation on a helicopter for dynamic testing of the rotor blade, and/or to installation in a whirl tower or other facility for dynamic testing of the rotor blade, as indicated at 252. If further dynamic testing is required, further adjustments to the balance of the rotor blade may be implemented.

As mentioned and as indicated at 232, some methods optionally may include performing dynamic testing of a rotor blade, such as on a rotor blade that was modeled utilizing method 230 or a variation thereon, including a rotor blade whose balance was adjusted following dynamic simulation and prediction of an updated weight balance. The dynamic testing may therefore be performed to acquire measured dynamic rotational data associated with the rotor blade being tested, as indicated at 234. Measured dynamic rotational data additionally or alternatively may be described as flight data associated with a rotor blade.

Dynamic testing may be performed by utilizing dynamic testing equipment 108, as discussed herein. Accordingly, such data as (i) angular deflections of the rotor blade at one or more rotational speeds and/or at one or more collective pitch angles, (ii) twisting of the rotor blade at one or more rotational speeds and/or at one or more collective pitch angles, (iii) relative translation, or height, data of various portions (e.g., tip region, hub region, body region, portions thereof, portions corresponding to the volumes of the three-dimensional model, etc.) of the rotor blade at one or more rotational speeds and/or at one or more collective pitch angles, such as in relation to the rotor blade when not being rotated, when being rotated at various other speeds, and/or in relation to a corresponding master rotor blade, (iv) surface characteristics of the rotor blade at one or more rotational speeds and/or at one or more collective pitch angles, (v) surface strains at one or more positions on the rotor blade at one or more rotational speeds and/or at one or more collective pitch angles, (vi) torsion loads at one or more positions on the rotor blade at one or more rotational speeds and/or at one or more collective pitch angles, (vii) bending and other moment loads at one or more positions on the rotor blade at one or more rotational speeds and/or at one or more collective pitch angles, (viii) etc. may be acquired during dynamic testing 232. These same data also may be acquired, predicted, or otherwise calculated during dynamic simulation 242, discussed below.

Upon acquisition of dynamic flight data associated with a rotor blade, such as a modeled rotor blade, the flight data may be associated with the modeled rotor blade in database 238. Accordingly, a record of the differences between simulated, or predicted, flight data 244 and actual flight data 234 may be made. Moreover, the simulation process, including the dynamic simulation software, may be updated to reflect these differences. Additionally or alternatively, a record of the specific weight balance adjustments that may have been made at 260 and the resulting flight data 234 may be accessed and referenced with respect to future modeled rotor blades. In other words, the database and its resources for predicting weight balance adjustments for future modeled rotor blades may be improved as additional dynamic testing is performed on modeled rotor blades and the results are included in the database. A goal of developing the database may be to reduce the total number of actual flight tests required to fine tune the weight balance of a rotor blade to a desired weight balance, and in some circumstances no dynamic testing may be required for a modeled rotor blade before having the rotor blade proceed to installation and use in the field.

Referring back to the decision block at 250, additionally or alternatively, as indicated at 254, the model of the rotor blade may be adjusted to account for the proposed configuration that was determined at 248. That is, the balance of the rotor blade itself is not necessarily adjusted at this step, but rather the model of the rotor blade may be adjusted. Then, a dynamic simulation 242 may be performed on the virtually adjusted rotor blade, resulting in updated predicted flight data. Again, the database may be updated with this information. If the updated flight data matches, or otherwise corresponds to, a desired balance, such as associated with a master blade, then the balance of the rotor blade may be appropriately balanced and proceed to flight and/or dynamic testing. However, in some circumstances the subsequent dynamic simulation may not result in predicted flight data that appropriately matches desired characteristics of a master blade, in which case a further virtual adjustment of the rotor blades balance may be made and simulated.

Figure 1:
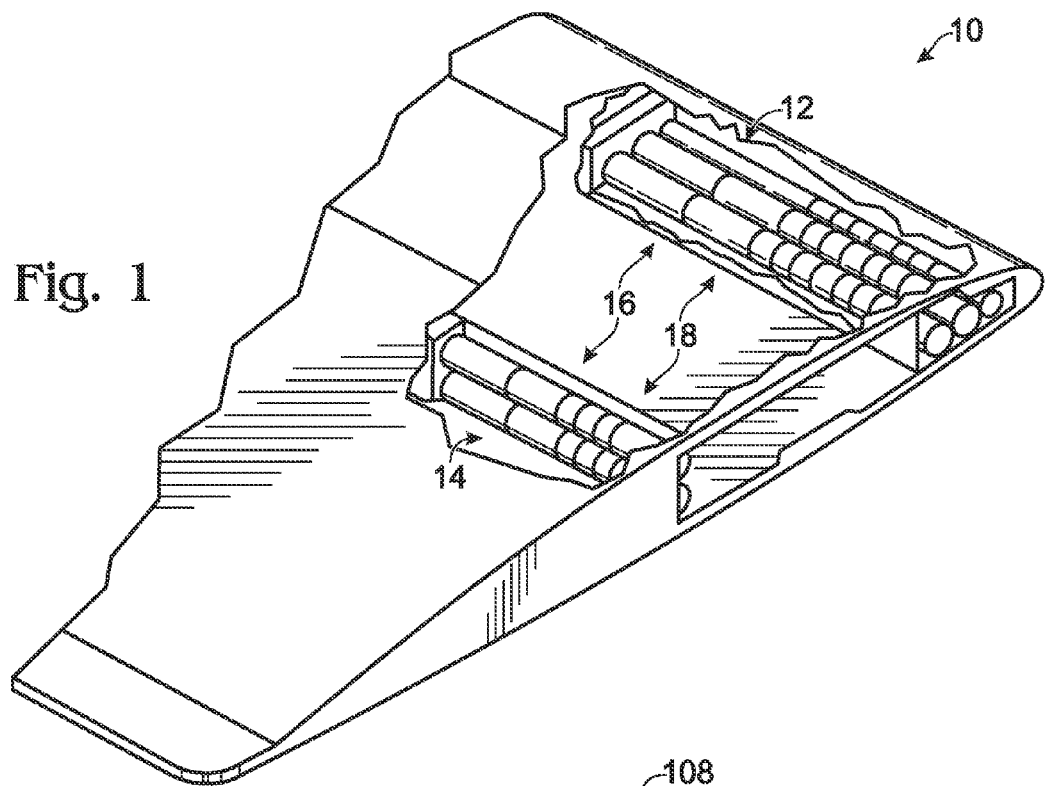
FIG. 1 is a schematic cut-away isometric view of a portion of a helicopter rotor blade.

Database 238 continuously or periodically may be updated with additional data associated with predicted flight data, modeled rotor blades, actual dynamic testing results, etc. Accordingly, over time, the database continues to grow with data associated with various mass distributions of rotor blades together with simulated and/or actual results of weight balance adjustments to those mass distributions. Therefore, the iterations of simulations and/or actual dynamic testing of a modeled rotor blade may be reduced for any given rotor blade. Ideally, and eventually, a single rotor blade that is modeled according to a method according to the present disclosure, such as according to a method 230, may have its balance adjusted only once prior to installation and flight on an actual helicopter. With reference to FIG. 3, the database is referenced with respect to a modeled rotor blade to determine an ideal updated balance configuration to match a desired master blade, as indicated at 256. This results in a proposed weight configuration for the modeled rotor blade, as indicated at 258, at which point, the rotor blade's balance may be appropriately configured, as indicated at 260, and the rotor blade may proceed to flight, as indicated at 252. One or both of the chord-wise balance and/or span-wise balance of the rotor blade may be adjusted, and the discussion herein with respect to FIG. 1 provides an illustrative, non-exclusive example of a weight for rotor blade weight adjustment. In some situations, the initial flight may include dynamic testing of the rotor blade to ensure that the desired balance was appropriately achieved. In other situations, the initial flight may not include dynamic testing of the rotor blade, and the rotor blade and associated helicopter may be put into service.

Illustrative, non-exclusive examples of inventions according to the present disclosure, including machine tools and methods, are described in the following enumerated paragraphs.

A A method comprising:
processing by a computer density data of a rotor blade to produce a density map of the rotor blade.

A1 The method of paragraph A, further comprising: prior to the processing, scanning by a scanner the rotor blade to acquire the density data.

A1.1 The method of paragraph A1, wherein the scanning includes scanning the rotor blade with a computer densitometry system.

A1.2 The method of paragraph A1, wherein the scanning includes scanning the rotor blade with a computer tomography system.

A1.3 The method of paragraph A1, wherein the scanning includes scanning the rotor blade with an X-ray computed tomography system.

A1.4 The method of any of paragraphs A1-A1.3, wherein the scanning includes scanning the rotor blade at a rate of at least 15, 25, 50, 100, or 1,000 millimeters of the length of the rotor blade per minute.

A2 The method of any of paragraphs A-A1.4, wherein the scanning includes scanning at a lower resolution than at least one of 1, 10, 100, 1,000, or 10,000 microns.

A3 The method of any of paragraphs A-A2, wherein the density map is represented by a raster image of the rotor blade.

A4 The method of any of paragraphs A-A3, wherein the density map is represented by a grayscale raster image of the rotor blade.

A5 The method of any of paragraphs A-A4, wherein the density map is represented by a three-dimensional construct of slices of the rotor blade.

A6 The method of any of paragraphs A-A5, further comprising:
merging by a computer the density map with a three-dimensional model of the rotor blade to define a relative density distribution model of the rotor blade.

A6.1 The method of paragraph A6, wherein the three-dimensional model includes a finite plurality of volumes within an outer contour of the rotor blade.

A6.1.1 The method of paragraph A6.1, wherein the merging includes assigning a density value to each volume of the finite plurality of volumes, wherein the density values represent the relative densities between the finite plurality of volumes.

A6.2 The method of any of paragraphs A6-A6.1.1, further comprising:
merging by a computer the relative density model with measured weight data of the rotor blade to define a relative mass distribution model of the rotor blade.

A6.2.1 The method of paragraph A6.2, further comprising:
merging by a computer the relative mass distribution model of the rotor blade with rotational considerations to define a dynamic model of the rotor blade.

A6.2.1.1 The method of paragraph A6.2.1, further comprising:
accessing by a computer a database of prior dynamic models of prior rotor blades and comparing the dynamic model of the rotor blade to the prior dynamic models; and
based at least in part on the comparing, predicting by a computer a proposed weight adjustment to the rotor blade to match a desired weight distribution.

A6.2.1.1.1 The method of paragraph A6.2.1.1, further comprising:
adjusting the balance of the rotor blade based at least in part on the predicting to have an updated rotor blade.

A6.2.1.1.1.1 The method of paragraph A6.2.1.1.1, further comprising:
updating by a computer the dynamic model of the rotor blade with measured dynamic rotational data of the updated rotor blade to define an updated dynamic model of the rotor blade.

A6.2.2 The method of any of paragraphs A6.2-A6.2.1.1.1, further comprising:
predicting by a computer dynamic flight data of the rotor blade based at least in part on the relative mass distribution within the rotor blade.

A6.2.3 The method of any of paragraphs A6.2-A6.2.2, further comprising:
comparing by a computer the relative mass distribution model of the rotor blade with pre-existing mass distribution models of prior tested rotor blades; and based on the comparing, determining by a computer predicted dynamic characteristics of the rotor blade.

A6.2.4 The method of any of paragraphs A6.2-A6.2.3, further comprising: comparing by a computer the relative mass distribution model of the rotor blade with pre-existing mass distribution models of prior tested rotor blades; and based on the comparing, determining by a computer a proposed updated weight distribution for the rotor blade to match a desired weight distribution.

A6.2.4.1 The method of paragraph A6.2.4, further comprising:

predicting by a computer predicted dynamic flight data of the rotor blade having the updated weight distribution based at least in part on the relative mass distribution of the rotor blade.

A6.2.5 The method of any of paragraphs A6.2.3-A6.2.4.1, further comprising:

based on the determining, outputting by a computer instructions for adjusting the weight distribution of the rotor blade to a desired weight distribution balance.

A6.2.5.1 The method of paragraph A6.2.5, further comprising:

adjusting the weight balance of the rotor blade to the desired weight distribution balance.

A7 The method of any of paragraphs A-A6.2.5.1, further comprising the method of any of paragraphs B-B6.

A8 The method of any of paragraphs A-A7, wherein the method utilizes the system of any of paragraphs D-D2.

B A method comprising:

accessing with a computer a database, wherein the database includes dynamic models that are based on relative mass distribution models of rotor blades;

based on the accessing, determining by a computer a proposed weight distribution of a rotor blade to be balanced.

B1 The method of paragraph B, wherein the determining is based at least in part on simulating by a computer dynamic flight data of the rotor blade to be balanced.

B1.1 The method of paragraph B1, further comprising:

based on the determining, simulating by a computer dynamic flight data of the rotor blade to be balanced having the proposed weight distribution of the rotor blade to be balanced.

B2 The method of any of paragraphs B-B1.1, further comprising:

based at least in part on the proposed weight distribution of the rotor blade to be balanced, outputting by a computer instructions for adjusting the balance of the rotor blade to be balanced to the proposed weight distribution.

B3 The method of any of paragraphs B-B2, further comprising:

adjusting the rotor blade to be balanced to have the proposed weight distribution.

B4 The methods of any of paragraphs B-B3, further comprising one or more steps of the methods of any of paragraphs A-A7.

B5 The method of any of paragraphs B-B4, further comprising the method of any of paragraphs A-A7.

B6 The method of any of paragraphs B-B5, wherein the method utilizes the software of any of paragraphs C-C1.

B7 The method of any of paragraphs B-B6, wherein the method utilizes the system of any of paragraphs D-D2.

C Computer readable storage media including computer-executable instructions that, when executed, direct a computer to perform the method of any of paragraphs A-B5.

C1 A computer comprising:

a memory device including computer-executable instructions that, when executed, direct a computer to perform the method of any of paragraphs A-B5.

D A system comprising:

a computer configured to perform the method of any of paragraphs A-B7.

D1 The system of paragraph D, wherein the computer includes a memory device including computer-executable instructions that, when executed, direct the computer to perform the method of any of paragraphs A-B6.

D2 The system of any of paragraphs D-D1, further comprising:

one or more of a computer densitometry system, a computer tomography system, or an X-ray computed tomography system.

The various disclosed elements of systems disclosed herein and the various disclosed steps of methods disclosed herein are not required to all systems and methods according to the present disclosure. Moreover, one or more of the various elements and steps disclosed herein may define independent inventive subject matter that is separate and apart from the whole of a disclosed system or method. Accordingly, such inventive subject matter is not required to be associated with the specific systems and methods that are expressly disclosed herein, and such inventive subject matter may find utility in systems and/or methods that are not expressly disclosed herein.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

The disclosure set forth above encompasses multiple distinct inventions with independent utility. While each of these inventions has been disclosed in its preferred form or method, the specific alternatives, embodiments, and/or methods thereof as disclosed and illustrated herein are not to be considered in a limiting sense, as numerous variations are possible. The present disclosure includes all novel and non-obvious combinations and subcombinations of the various elements, features, functions, properties, methods, and/or steps disclosed herein. Similarly, where any disclosure above or claim below recites "a" or "a first" element, step of a method, or the equivalent thereof, such disclosure or claim should be understood to include incorporation of one or more such elements or steps, neither requiring nor excluding two or more such elements or steps.

It is believed that the following claims particularly point out certain combinations and subcombinations that are directed to one of the disclosed inventions and are novel and non-obvious. Inventions embodied in other combinations and subcombinations of features, functions, elements, properties, methods, and/or steps may be claimed through amendment of the present claims or presentation of new claims in this or a related application. Such amended or new claims, whether they are directed to a different invention or directed to the same invention, whether different, broader, narrower, or equal in scope to the original claims, also are regarded as within the subject matter of the inventions of the present disclosure.

The invention claimed is:

1. A method comprising:
   receiving by a computer density data of a rotor blade, wherein the density data was acquired by a scanner;
   processing by a computer the density data to produce a density map of the rotor blade; and
   merging by a computer the density map with a three-dimensional model of the rotor blade to define a relative density distribution model of the rotor blade, wherein the three-dimensional model includes a finite plurality of volumes within an outer contour of the rotor blade.

2. The method of claim 1, further comprising:
   prior to the receiving and the processing, scanning by a scanner the rotor blade to acquire the density data.

3. The method of claim 2, wherein the scanning includes scanning the rotor blade at a rate of at least 15 millimeters of the length of the rotor blade per minute.

4. The method of claim 2, wherein the scanning includes scanning at a resolution in the range of 10-10,000 microns.

5. The method of claim 1, wherein the merging includes assigning a density value to each volume of the finite plurality of volumes, wherein the density values represent the relative densities between the finite plurality of volumes.

6. The method of claim 1, further comprising:
   merging by a computer the relative density model with measured weight data of the rotor blade to define a relative mass distribution model of the rotor blade.

7. The method of claim 6, further comprising:
   merging by a computer the relative mass distribution model of the rotor blade with rotational considerations to define a dynamic model of the rotor blade.

8. The method of claim 7, further comprising:
   accessing by a computer a database of prior dynamic models of prior rotor blades and comparing the dynamic model of the rotor blade to the prior dynamic models; and
   based at least in part on the comparing, predicting by a computer a proposed weight adjustment to the rotor blade to match a desired weight distribution.

9. The method of claim 8, further comprising:
   adjusting the balance of the rotor blade based at least in part on the predicting to have an updated rotor blade.

10. The method of claim 9, further comprising:
    updating by a computer the dynamic model of the rotor blade with measured dynamic rotational data of the updated rotor blade to define an updated dynamic model of the rotor blade.

11. The method of claim 6, further comprising:
    predicting by a computer dynamic flight data of the rotor blade based at least in part on the relative mass distribution of the rotor blade.

12. The method of claim 6, further comprising:
    comparing by a computer the relative mass distribution model of the rotor blade with pre-existing mass distribution models of prior tested rotor blades; and
    based on the comparing, determining by a computer predicted dynamic characteristics of the rotor blade.

13. The method of claim 6, further comprising:
    comparing by a computer the relative mass distribution model of the rotor blade with pre-existing mass distribution models of prior tested rotor blades; and
    based on the comparing, determining by a computer a proposed updated weight distribution for the rotor blade to match a weight distribution of a master blade.

14. The method of claim 13, further comprising:
    predicting by a computer predicted dynamic flight data of the rotor blade having the updated weight distribution based at least in part on the relative mass distribution of the rotor blade.

15. The method of claim 13, further comprising:
    based on the determining, outputting by a computer instructions for adjusting the weight distribution of the rotor blade to match the weight distribution of the master blade; and
    adjusting the weight balance of the rotor blade to match the weight distribution of the master blade.

16. A system comprising:
    a computer configured to perform the method of claim 1; and
    a scanner configured to acquire the density data of the rotor blade.

17. The method of claim 1, wherein the finite plurality of volumes includes one or more volumes corresponding to critical regions of the rotor blade and one or more volumes corresponding to non-critical regions of the rotor blade, and wherein the one or more volumes corresponding to critical regions of the rotor blade are smaller than the one or more volumes corresponding to non-critical regions of the rotor blade.

18. A method comprising:
    accessing with a computer a database, wherein the database includes dynamic models that are based on relative mass distribution models of rotor blades, wherein the relative mass distribution models are based at least in part on data acquired from scanning the rotor blades;
    based on the accessing, determining by a computer a proposed weight distribution of a rotor blade to be balanced.

19. The method of claim 18, wherein the determining is based at least in part on simulating by a computer dynamic flight data of the rotor blade to be balanced.

20. A method comprising:
    processing by a computer density data of a rotor blade to produce a density map of the rotor blade; and
    prior to the processing, scanning by a scanner the rotor blade to acquire the density data, wherein the scanning includes scanning at a resolution in the range of 10-10,000 microns.

* * * * *